(12) United States Patent
Kostinko et al.

(10) Patent No.: US 6,869,595 B2
(45) Date of Patent: Mar. 22, 2005

(54) ABRASIVE COMPOSITIONS FOR CLEAR TOOTHPASTE

(75) Inventors: John A. Kostinko, Bel Air, MD (US); William C. Fultz, Rising Sun, MD (US); Patrick D. McGill, Darlington, MD (US)

(73) Assignee: J.M. Huber Corporation, Edison, NJ (US)

( * ) Notice: Subject to any disclaimer, the term of this patent is extended or adjusted under 35 U.S.C. 154(b) by 0 days.

(21) Appl. No.: 10/292,986

(22) Filed: Nov. 13, 2002

(65) Prior Publication Data

US 2003/0133882 A1 Jul. 17, 2003

Related U.S. Application Data

(63) Continuation-in-part of application No. 10/029,510, filed on Dec. 21, 2001, now abandoned.

(51) Int. Cl.$^7$ ............................. A61K 7/16; A61K 7/18
(52) U.S. Cl. ........................ 424/49; 423/335; 423/339; 51/308
(58) Field of Search ............................ 424/49; 423/335, 423/339; 51/308

(56) References Cited

U.S. PATENT DOCUMENTS 4,992,251 A * 2/1991 Aldcroft et al. ............ 423/335

* cited by examiner

*Primary Examiner*—Frederick F. Krass
(74) *Attorney, Agent, or Firm*—Carlos Nieves; David Mitchell Goodrich; William Parks

(57) ABSTRACT

A transparent dentifrice is provided that has excellent abrasive performance. The dentifrice comprises from about 10 wt % to about 13 wt % water, and an abrasive, low-structure, precipitated silica having: a refractive index of from about 1.439 to 1.450, an oil absorption of from about 90 ml/100 g to about 120 ml/100 g, a light transmittance of greater than about 60%; and a Brass Einlehner abrasion value of less than about 5 mg loss/100,000 rev. Additionally the dentifrice has: a haze value of less than about 50; an RDA of about 50 to 200; and a refractive index of from about 1.439 to 1.450.

13 Claims, 1 Drawing Sheet

ABRASIVE COMPOSITIONS FOR CLEAR TOOTHPASTE

CROSS-REFERENCE TO RELATD APPLICATION

This is a continuation in part application of U.S. patent application Ser. No. 10/029,510, filed Dec. 21, 2001 now abandoned, entitled "Dentifrice Compositions".

BACKGROUND OF THE INVENTION

Precipitated silicas find use in a broad range of manufactured products ranging from cosmetic and food products to industrial coatings to elastomeric materials, such as tires. Silicas are particularly useful in dentifrice products (such as toothpastes) where they function as abrasives and thickeners. Because of this functional versatility, and also because silicas, when compared to other dentifrice abrasives (notably alumina and calcium carbonate), have a relatively high compatibility with active ingredients like fluoride, there is a strong desire among toothpaste and dentifrice formulators to include them in their products.

However, it can be difficult to incorporate abrasive silicas into transparent dentifrice products. These transparent toothpaste products have become increasingly popular in recent years because of their greater appeal to some consumers and because they allow manufacturers to impart increased distinctiveness to their product. In order to produce a silica-containing transparent toothpaste, it is necessary that the silica's refractive index closely matches the refractive index of the toothpaste matrix, and that the silica has a high degree of light transmittance. Furthermore, in order to provide dental hygiene benefits, the silica must have sufficient abrasivity to provide cleaning of the tooth surfaces when incorporated into a dentifrice. Lastly, when incorporated in a transparent dentifrice, the silica should provide sufficient dentifrice viscosity build to make the transparent dentifrice convenient for consumer use.

Because the refractive index of the silica must match the refractive index of the toothpaste matrix in order for the toothpaste to be transparent, typically the concentration of water in the toothpaste must be maintained at relatively low levels. Water generally has a far lower refractive index than silica, glycerin and sorbitol: commercially available precipitated silicas have a refractive index of about 1.438 to 1.451, while water has a refractive index of 1.332, 98% glycerin has a refractive index of 1.472 and 70% sorbitol has a refractive index of 1.456. As the toothpaste's water concentration increases, the refractive index of the toothpaste decreases, and thus, in order for the refractive index of the silica to match the refractive index of the toothpaste, the water concentration in the toothpaste must be minimized. This is undesirable because water is generally the least expensive toothpaste component, and decreases in water concentration are normally offset by increases in humectant concentration (which is quite expensive). Thus, decreasing water concentration will cause a corresponding increase in the toothpaste unit cost.

Furthermore, an abrasive silica is an indispensable ingredient in a transparent toothpaste for providing effective dental cleaning performance. Unfortunately adding an abrasive silica can reduce the transparency of the overall toothpaste product because of its low degree of transmittance and high refractive index. Because of the silica's high refractive index, it is often necessary to reduce the water concentration while increasing the humectant concentration, which results in a significant increase in product cost.

Another consideration for producing a transparent toothpaste is related to the toothpaste viscosity. Most commercial toothpastes have a viscosity range of between 250,000 cps to 1,000,000 cps. When the viscosity is less than 250,000 cps, the toothpaste is very thin and has poor stand-up characteristics, so that the toothpaste sinks into the bristles of the toothbrush and drips from the brush. When the viscosity is greater than 1,000,000 cps, the toothpaste becomes very difficult to squeeze from the tube and less likely to have good dispersion in the mouth.

Typically, the viscosity build of a toothpaste is controlled through the use of silica, or gelling agents, such as polysaccharides or carboxymethyl cellulose. The gelling agent is usually present in low concentrations of about 0.1 to 1.5 wt % of the toothpaste composition, because higher concentrations of gelling agents can cause problems with product dispersion, rheology, and lumping. Because the gelling agent can only be used in these low concentrations, most toothpaste formulations are dependent on the silica component to increase the viscosity build of the toothpaste to a satisfactory level. But if a silica with low structure and low oil absorption is used, then high loading levels of silica are required to build the toothpaste to the required viscosity. By contrast, very high structure silica provides good viscosity build, but does not provide adequate abrasiveness for tooth cleaning.

Given the foregoing, there is a continuing need for a silica composition that not only provides excellent abrasive performance and high oil absorption (allowing for good viscosity build), but also has good optical properties such as a relatively high degree of transmittance, and an index of refraction that is sufficiently low, such that the silica can be included in a transparent toothpaste composition having a relatively high concentration of water.

BRIEF SUMMARY OF THE INVENTION

The invention includes an amorphous precipitated silica composition, the silica composition having a refractive index of from about 1.439 to 1.450, a light transmittance of greater than about 60%; and a Brass Einlehner abrasion value of less than about 5 mg loss/100,000 rev.

The invention also includes a dentifrice comprising a premix containing no silica, wherein the premix has a refractive index of from about 1.439 to 1.450. The dentifrice also comprises about 0.01 wt % to about 35 wt % of an abrasive silica, a RDA of greater than about 50, a haze value of less than about 50, and a viscosity of greater than about 425,000 cps.

The invention also includes a method of preparing a dentifrice comprising the steps of preparing a premix, which contains no silica and has a refractive index of from about 1.439 to 1.450, and mixing silica with the premix to form a dentifrice having an RDA of greater than about 50.

BRIEF DESCRIPTION OF THE DRAWING

The foregoing summary, as well as the following detailed description of preferred embodiments of the invention, will be better understood when read in conjunction with the appended drawing. It should be understood, however, that the invention is not limited to the precise physical relationships shown in the drawings.

DETAILED DESCRIPTION OF THE INVENTION

Figure 1:
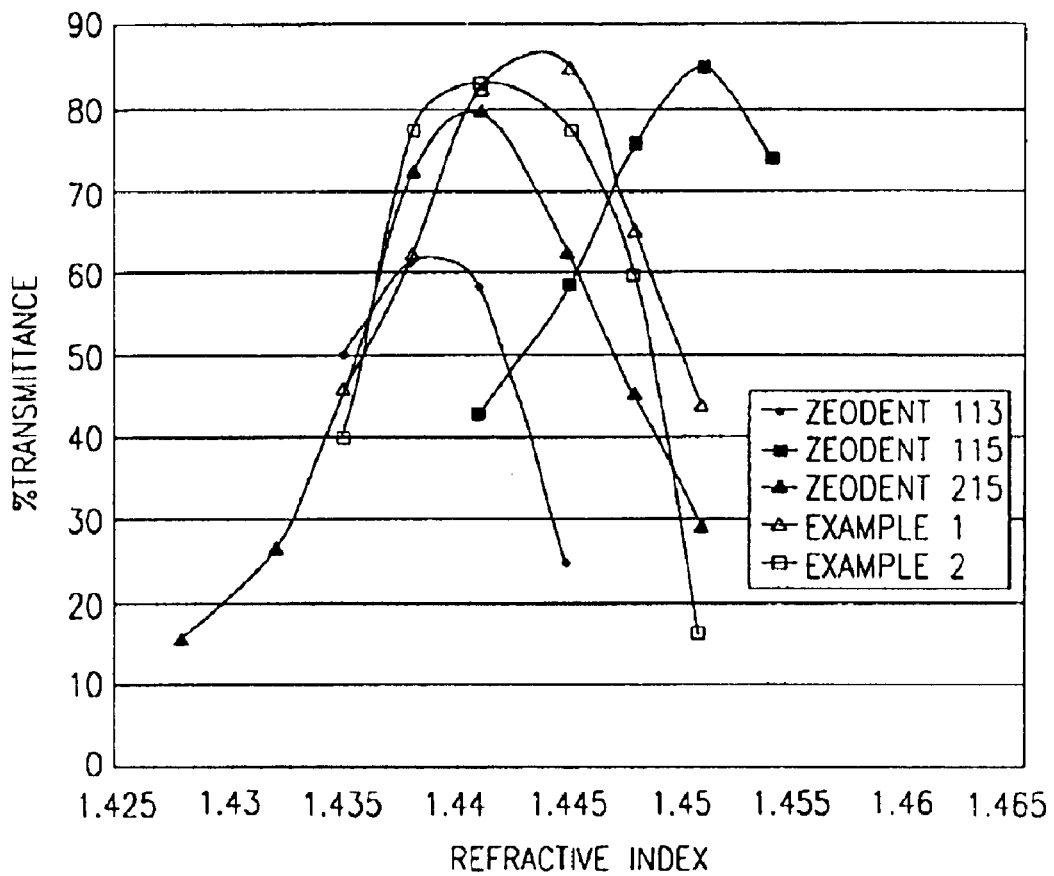
FIG. 1 is a curve that plots the relationship between the degree of light transmittance ("% Transmittance") versus the refractive index for precipitated silicas prepared according to the present invention and comparative prior art silica abrasives.

All parts, percentages and ratios used herein are expressed by weight unless otherwise specified. All documents cited herein are incorporated by reference. The following describes preferred embodiments of the present invention, which provides silica for use in dentifrices, such as toothpastes. While the optimal use for this silica is in dentifrices, this silica may also be used in a variety of other consumer products By "mixture" it is meant any combination of two or more substances, in the form of, for example without intending to be limiting, a heterogeneous mixture, a suspension, a solution, a sol, a gel, a dispersion, or an emulsion.

By "transparent", it is meant transmitting light so that images can be seen as if there were no intervening material.

By "dentifrices" it is meant oral care products such as, without intending to be limiting, toothpastes, tooth powders and denture creams.

By "low-structured silica" it is meant that the silica material has an oil absorption of between about 90 ml/100 g and 120 ml/100 g.

By "viscosity build" it is meant increasing dentifrice viscosity as measured by a Brookfield viscometer and is expressed in centipoise (cps)

The present invention relates to amorphous, low-structure precipitated silica compositions, also known as silicon dioxide, or $SiO_2$, which impart improved cleaning and abrasive characteristics when included within a toothpaste or dentifrice. Because they have a unique combination of low refractive index, high degree of light transmittance, medium abrasiveness and provide significant dentifrice viscosity build, the silicas of the present invention are particularly useful for formulating low-cost, transparent toothpaste that has a relatively high concentration of water.

To ensure good cleaning performance a sufficient amount of abrasive silica should be added to a toothpaste composition so that the radioactive dentin abrasion ("RDA") value of the toothpaste is between about 50 and 200. At a RDA of less than 50, the cleaning benefits of the toothpaste will be minimal, while at a RDA of greater than 200, there is serious risk that the toothpaste will be so abrasive that it may damage the tooth dentin along the gum line. Most commercial toothpaste products today have a RDA in the range of 50 to 150, with the average being exactly in the middle around 100. Preferably, the dentifrice should have a RDA value of at least about 50, such as between 70 and 120, such as between 90 and 110.

The RDA of a toothpaste is dependent on both the hardness (abrasiveness) of the abrasive and the concentration of the abrasive in the toothpaste. The RDA is measured by the method described in the article "The Measurement of the Abrasion of Human Teeth by Dentifrice Abrasives: A Test Utilizing Radioactive Teeth", Grabenstetter, R. J.; Broge, R. W.; Jackson, F. L.; and Radike, A. W. in the *Journal of Dental Research:* 37, 1060–68, 1958. Silica abrasivity can be measured by an Einlehner method, which is described in greater detail below. A correlation between silica Einlehner values, silica loading level in toothpaste and RDA values has been determined from historical data, and is summarized in equation (I) below:

$$RDA = (0.099003 \times E) + (0.773864 \times L) + (0.994414 \times E \times L) + \\ (-0.002875 \ E^2) + (-0.094783 \times L^2) + (3.417937) \quad (I)$$

where E is the brass Einlehner mg lost for an aqueous 10% silica slurry

L is the weight % silica loading in the toothpaste

For example, if a toothpaste contains 20 wt % of a silica having an Einlehner abrasion value (a measure of hardness, described in greater detail below) of about 6.0, then the toothpaste will have a RDA of about 100. A toothpaste having the same RDA value of about 100 could be obtained at a silica concentration level of about 6.5 wt % with a more abrasive silica, such as a silica having an Einlehner abrasion value of 15. Including this same silica having an Einlehner abrasion value of 15 at a 20 wt % concentration level would produce a toothpaste having a RDA of about 280.

Unfortunately, abrasive silicas that provide good abrasive cleaning performance, such as medium abrasive silica (i.e., those having Einlehner values of about 2.0 to 6.0) generally do not have both consistently good transparency properties (viz., high refractive index and a high degree of light transmittance) and also provide good viscosity build to a toothpaste composition. For example, a medium abrasive silica such as Zeodent® 215 silica (available from the J. M. Huber Corp., Edison, N. J.) provides good abrasive cleaning, and has an acceptably low refractive index, as well as an acceptable degree of light transmittance; but it has a low oil absorption and is thus less good at providing viscosity build in a toothpaste formulation. The relationship between the "structure" type, oil absorption, and viscosity building performance of a silica is discussed in greater detail in the article "Cosmetic Properties and Structure of Fine-particle Synthetic Precipitated Silicas", S. K. Wason, in *Journal of Soc. Cosmet. Chem.*, Vol. 29, (1978), pp. 497–521.

By contrast, Zeodent® 115 silica (also available from J. M. Huber Corp.) has good abrasive cleaning performance, a higher oil absorption and a relatively high degree of light transmittance, but it has a high refractive index (e.g. Zeodent® 115 silica in Table II below).

However, by the present invention, abrasive amorphous silicas have been developed that not only have excellent abrasion performance but are also are suitable for inclusion in a transparent toothpaste. By controlling the amount of silicate initially charged into the reactor ("excess silicate"), the batch reaction-digestion temperature profile, the digest time, addition rate, and batch final pH, a silica abrasive may be produced that has a high oil absorption (and thus good viscosity build) as well as relatively low refractive index and high degree of light transmittance. When incorporated into a transparent toothpaste composition, the toothpaste is sufficiently abrasive to provide good cleaning benefits while also having a viscosity that makes it convenient and easy to use.

The silica compositions of the present invention are prepared according to the following process. In this process, an aqueous solution of an alkali silicate, such as sodium silicate, is charged into a reactor, such as a reactor equipped with mixing means adequate to ensure a homogeneous mixture, and the aqueous solution of an alkali silicate in the reactor preheated to a temperature of between about 65° C. and about 100° C. Preferably, the alkali silicate aqueous solution has an alkali silicate concentration of approximately 8.0 to 35 wt %, such as from about 8.0 to about 15 wt %. Preferably the alkali silicate is a sodium silicate with a $SiO_2$:$Na_2O$ ratio of from about 1 to about 3.5, such as about 2.4 to about 3.4. The quantity of alkali silicate charged into the reactor is about 10 wt % to 20 wt % of the total silicate used in the batch. Optionally, an electrolyte, such as sodium sulfate solution, may be added to the reaction medium To the reactor is then simultaneously added: (1) an aqueous solution of acidulating agent or acid, such as sulfuric acid, and (2) additional amounts of an aqueous solution containing the same species of alkali silicate as is in the reactor, the aqueous solution being preheated to a temperature of about 65° C. to about 100° C. The aqueous acidulating agent solution preferably has a concentration of acidulating agent of about 6 to 35 wt %, such as about 9.0 to about 15 wt %. The simultaneous addition is continued until about 40% to 60% of the total batch alkali silicate is added, then the temperature is increased about 3° C. for the remainder of the precipitation reaction and digest time. The extent of the temperature increase varies depending on the temperature of the precipiation reaction. After all of the batch alkali silicate has been added, the acid solution addition continues until the reactor batch pH drops to between about 5.0 to about 6.0.

After the inflows of the acidulating agent and the alkali silicate are stopped, the reactor batch allowed to age or "digest" for between 5 minutes to 30 minutes, with the reactor batch being maintained at a constant pH. After the completion of digestion, the reaction batch is filtered and washed with water to remove excess by-product inorganic salts until the wash water from the silica filter cake obtains a conductivity of less than about 2000 $\mu$mhos. Because the conductivity of the silica filtrate is proportional to the inorganic salt by-product concentration in the filter cake, then by maintaining the conductivity of the filtrate to be less than 2000 $\mu$mhos, the desired low concentration of inorganic salts, such as $Na_2SO_4$ in the filter cake may be obtained.

The silica filter cake is slurried in water, and then dried by any conventional drying techniques, such as spray drying, to produce a precipitated silica containing from about 3 wt % to about 50 wt % of moisture. The precipitated silica may then be milled to obtain the desired particle size of between about 5 $\mu$m to 25 $\mu$m, such as about 5 $\mu$m to about 15 $\mu$m.

This abrasive, amorphous precipitated silica may then be incorporated into a dentifrice composition, e.g., a toothpaste.

In addition to the abrasive component, the dentifrice may also contain several other ingredients such as humectants, thickening agents, (also sometimes known as binders, gums, or stabilizing agents), antibacterial agents, fluorides, sweeteners, and surfactants.

Humectants serve to add body or "mouth texture" to a dentifrice as well as preventing the dentifrice from drying out. Suitable humectants include polyethylene glycol (at a variety of different molecular weights), propylene glycol, glycerin (glycerol), erythritol, xylitol, sorbitol, mannitol, lactitol, and hydrogenated starch hydrolyzates, as well as mixtures of these compounds.

Thickening agents are useful in the dentifrice compositions of the present invention to provide a gelatinous structure that stabilizes the toothpaste against phase separation. Suitable thickening agents include silica thickener, starch, glycerite of starch, gum karaya (sterculia gum), gum tragacanth, gum arabic, gum ghatti, gum acacia, xanthan gum, guar gum, veegum, carrageenan, sodium alginate, agar-agar, pectin, gelatin, cellulose, cellulose gum, carboxymethyl cellulose, hydroxyethyl cellulose, hydroxypropyl cellulose, hydroxymethyl, hydroxymethyl carboxypropyl cellulose, methyl cellulose, ethyl cellulose, sulfated cellulose, as well as mixtures of these compounds. Typical levels of binders are from about 0 wt % to about 15 wt % of a toothpaste composition.

Antibacterial agents may be included to reduce the presence of microorganisms to below known harmful levels. Suitable antibacterial agents include benzoic acid, sodium benzoate, potassium benzoate boric acid phenolic compounds such as betanapthol, chlorothymol, thymol, anethole, eucalyptol, carvacrol, menthol, phenol, amylphenol, hexylphenol, heptylphenol, octylphenol, hexylresorcinol, laurylpyridinium chloride, myristylpyridinium chloride, cetylpyridinium fluoride, cetylpyridinium chloride, cetylpyridinium bromide. If present, the level of antibacterial agent is preferably from about 0.1 wt % to about 5 wt % of the toothpaste composition.

Sweeteners may be added to the toothpaste composition to impart a pleasing taste to the product. Suitable sweeteners include saccharin (as sodium, potassium or calcium saccharin), cyclamate (as a sodium, potassium or calcium salt), acesulfane-K, thaumatin, neohisperidin dihydrochalcone, ammoniated glycyrrhizin, dextrose, levulose, sucrose, mannose, and glucose.

The toothpaste will also preferably contain fluoride salts to prevent the development and progression of dental caries. Suitable fluoride salts include sodium fluoride, potassium fluoride, calcium fluoride, zinc fluoride, stannous fluoride, zinc ammonium fluoride, sodium monofluorophosphate, potassium monofluorophosphate, laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, and sodium monofluorophosphate. Typical levels of fluoride salts are from about 0.1 wt % to about 5 wt %.

Condensed phosphates may be one or a combination of tetrasodium pyrophosphate, tetrapotassium pyrophosphate, disodium dihydrogen pyrophosphate, trisodium monohydrogen pyrophosphate, pentasodium tripolyphosphate and sodium polymetaphosphate, singly or in combinations thereof.

Surfactants may also be included as additional cleansing and foaming agents, and may be selected from anionic surfactants, zwitterionic surfactants, nonionic surfactants, amphoteric surfactants, and cationic surfactants. Anionic surfactants are preferred, such as metal sulfate salts, such as sodium lauryl sulfate.

The dentifrices disclosed herein may also a variety of additional ingredients such as desensitizing agents, healing agents, other caries preventative agents, chelating/sequestering agents, vitamins, amino acids, proteins, other anti-plaque/anti-calculus agents, opacifiers, antibiotics, anti-enzymes, enzymes, pH control agents, oxidizing agents, antioxidants, whitening agents and preservatives.

Finally, water provides the balance of the composition in addition to the additives mentioned. The water is preferably deionized and free of impurities. The dentifrice will comprise from about 10 wt % to about 13 wt % of water.

The invention will now be described in more detail with respect to the following, specific, non-limiting examples.

EXAMPLES 1–2

In Examples 1–2, silicas suitable for use in dentifrices as well as other products, were prepared according to the present invention. The quantities of reactants and the reactant conditions are set forth in Table 1, below. First, an aqueous solution containing 13.3 wt % of sodium silicate (having a 2.65 molar ratio of $SiO_2:Na_2O$) was charged into a reactor ("the excess silicate"), heated to 90° C. An aqueous solution of sulfuric acid (at a concentration of 11.4 wt %) and an aqueous solution of sodium silicate (at a concentration of 13.3 wt %, the sodium silicate having a 2.65 mole ratio, the solution heated to 85° C.) were then added simultaneously at the rates set forth in Table I. The silicate addition was stopped after 48 minutes and the acid addition continued until the reactor batch pH dropped to 7.0. When the reaction reached 7.0 pH, the acid rate was reduced to 10 GPM to adjust the reaction pH to 5.2 to 5.5. The batch temperature was then maintained at 93° C. for ten minutes, with the final pH adjusted and maintained at 5.2 to 5.5. The silica batch was then filtered and washed to form a filter cake having a conductivity of not more than about 1700 μmhos. The filter cake was then slurried with water and spray dried to a moisture content of between 8 to 12%. The spray dried product was hammer-milled to a particle size of between 8–15 μm.

The quantities of the reactants added and the processing parameters of the reactions are as follows:

TABLE I

| Example | Excess silicate (Gal.) | Silicate rate GPM | Acid rate GPM |
|---|---|---|---|
| 1 | 879 | 83.25 | 37.1 |
| 2 | 757 | 85.9 | 38.3 |

After being prepared as set forth above, several properties of the particulate silica, including 5% pH, % Sodium sulfate, oil absorption, the degree of light transmission ("% Transmittance"), refractive index, silica particle size, Einlehner abrasion, brightness, Moisture and % 325 mesh residue were then measured. The 5% pH is determined on a slurry of 5 g silica in 95 g water.

Sodium sulfate content is measured by conductivity of a known concentration of silica slurry. Specifically, 38 g silica wetcake sample is weighed into a one-quart mixer cup of a Hamilton Beach Mixer, Model Number 30, and 140 ml of deionized water is added. The slurry is mixed for 5 to 7 minutes, then the slurry is transferred to a 250-ml graduated cylinder and the cylinder filled to the 250-ml mark with deionized water, using the water to rinse out the mixer cup. The sample is mixed by inverting the graduated cylinder (covered) several times. A conductivity meter, such as a Cole Palmer CON 500 Model #19950-00, is used to determine the conductivity of the slurry. Sodium sulfate content is determined by comparison of the sample conductivity with a standard curve generated from known method-of-addition sodium sulfate/silica composition slurries.

The oil absorption was measured using linseed oil by the rubout method. In this test, oil is mixed with a silica and rubbed with a spatula on a smooth surface until a stiff putty-like paste is formed. By measuring the quantity of oil required to have a paste mixture, which will curl when spread out, one can calculate the oil absorption value of the silica—the value which represents the volume of oil required per unit weight of silica to completely saturate the silica sorptive capacity. Calculation of the oil absorption value was done as follows:

$$\text{Oil absorption} = \frac{\text{ml oil absorbed}}{\text{weight of silica, grams}} \times 100 \quad \text{(II)}$$

$$= \text{ml oil}/100 \text{ gram silica}$$

As a first step in measuring the refractive index ("RI") and degree of light transmission, a range of glycerin/water stock solutions (about 10) was prepared so that the refractive index of these solutions lies between about 1.428 and 1.46. The exact glycerin/water ratios needed depend on the exact glycerin used and is determined by the technician making the measurement. Typically, these stock solutions will cover the range of 70 wt % to 90 wt % glycerin in water. To determine Refractive Index, one or two drops of each standard solution is separately placed on the fixed plate of the refractometer (Abbe 60 Refractometer Model 10450). The covering plate is fixed and locked into place. The light source and refractometer are switched on and the refractive index of each standard solution is read.

Into separate 20 $cm^3$ bottles, accurately weigh 2.0±0.01 silica and add 18.0 g±0.01 of each respective stock glycerin/water solution. The bottles were then shaken vigorously to form silica dispersions, the stoppers removed from the bottles, and the bottles were placed in a desiccator, which was then evacuated with a vacuum pump.

The dispersions are de-aerated for 120 minutes and visually inspected for complete de-aeration. The %Transmittance ("%T") at 590 nm (Spectronic 20 D+) is measured after the samples return to room temperature (about 10 min), according to the manufacturer's operating instructions.

%Transmittance is measured on the silica/glycerin/water disperisons by placing an aliquot of each dispersion in a glass spectronic tube and reading the %T at 590 nm wavelength for each sample on a 0–100 scale. %Transmittance vs. RI of the stock solutions used is plotted on a curve, as shown in FIG. 1, for Example 1 and Example 3. The Refractive index of the silica is defined as the position (the ordinate or X value) of the plotted peak maximum on the %Transmittance vs. RI curve. The value of Y-axis (the abscissa) of the peak maximum is the %Transmittance of the silica.

The Mean Particle Size is determined using a Leeds and Northrup Microtrac II. A laser beam is projected through a transparent cell which contains a stream of moving particles suspended in a liquid. Light rays that strike the particles are scattered through angles that are inversely proportional to their sizes. The photodetector array measures the quantity of light at several predetermined angles. Electrical signals proportional to the measured light flux values are then processed by a microcomputer system to form a multi-channel histogram of the particle size distribution.

The Brass Einlehner (BE) Abrasion value was measured through the use of an Einlehner AT-1000 Abrader. In this test, a Fourdrinier brass wire screen is weighed and exposed to the action of a 10% aqueous silica suspension for a fixed number of revolutions, and the amount of abrasion is then determined as milligrams brass lost from the Fourdrinier wire screen per 100,000 revolutions. Disposable supplies required for this test (brass screens, wear plates and PVC tubing) are available from Duncan Associates, Rutland, Vt. and sold as an "Einlehner Test Kit". Specifically, brass screens (Phosphos Bronze P.M.) were prepared by washing in hot, soapy water (0.5% Alconox) in an ultrasonic bath for 5 minutes, then rinsed in tap water and rinsed again in a beaker containing 150 ml water set in an ultrasonic bath. The screen is rinsed again in tap water, dried in an oven set at 105° C. for 20 minutes, cooled in a desiccator and weighed. Screens were handled with tweezers to prevent skin oils from contaminating the screens. The Einlehner test cylinder is assembled with a wear plate and weighed screen (red line side down—not abraded side) and clamped in place. The wear plate is used for about 25 tests or until worn badly; the weighed screen is used only once.

A 10% silica slurry, prepared by mixing 100 g silica with 900 g deionized water, was poured into the Einlehner test cylinder. Einlehner PVC tubing was placed onto the agitating shaft. The PVC tubing has 5 numbered positions. For each test, the position of the PVC tubing is incremented until it has been used five times, then discarded. The Einlehner abrasion instrument is re-assembled and the instrument set to run for 87,000 revolutions. Each test takes about 49 minutes. After the cycle is completed, the screen is removed rinsed in tap water, placed in a beaker containing water and set in an ultrasonic bath for 2 minutes, rinsed with deionized water and dried in an oven set at 105° C. for 20 minutes. The dried screen is cooled in a desiccator and reweighed. Two tests are run for each sample and the results are averaged and expressed in mg lost per 100,000 revolutions. The result, measured in units of mg lost per 100,000 revolutions, for a 10% slurry can be characterized as the 10% brass Einlehner (BE) abrasion value.

To measure the brightness values, fine powder materials are pressed into a smooth surfaced pellet and are evaluated using a Technidyne Brightmeter S-5/BC. This instrument has a dual beam optical system where the sample is illuminated at an angle of 45°, and the reflected light viewed at 0°. It conforms to TAPPI test methods T452 and T646, and ASTM Standard D985. Powdered materials are pressed to about a 1 cm thick pellet with enough pressure to give a pellet surface that is smooth and flat and without loose particles or gloss.

To measure the moisture content of silica, the silica sample is dried for 2 hours at 105° C. and moisture determined by weight percent difference.

The %325 sieve residue, which measures the amount of "grit" in the toothpaste, may also be measured. Because, inter alia, the presence of grit gives consumers an unpleasant mouth feel, and because grit interferes with the dissolution of the toothpaste in the mouth, it is preferred to keep the %325 sieve residue as low as possible.

To measure the %325 sieve residue, weigh 50 g silica into a 1-liter beaker containing 500–600 ml water. Allow the silica to settle into the water, then mix well until all the material is dispersed. Adjust the water pressure through the spray nozzle (Fulljet 9.5, ⅜ G, 316 stainless steel, Spraying Systems Co.) to 20–25 psi. Hold the sieve screen cloth (325 mesh screen, 8" diameter) 4–6 inches below the nozzle and, while spraying, gradually pour the contents of the beaker onto the 325 mesh screen. Rinse the remaining material from the walls of the beaker and pour onto the screen. Wash for 2 minutes, moving the spray from side to side in the screen using a sweeping motion. After spraying for 2 minutes (all particles smaller than the screen opening should have passed through the screen), wash the residue retained on the screen to one side, and then transfer it into a pre-weighed aluminum weighing dish by washing with water from a squirt bottle. Use the minimum amount of water needed to be sure all the residue is transferred into the weighing dish. Allow the dish to stand 2–3 minutes (residue settles), then decant the clear water off the top. Place dish in an oven ("Easy-Bake" infrared oven or 105° C. oven) and dry until the residue sample is dried to a constant weight. Re-weigh the dry residue sample and dish.

Calculation of the %325 residue is done as follows:

$$\% \; 325 \; \text{residue} = \frac{\text{weight of residue}}{\text{sample weight, grams}} \times 100 \qquad (\text{II})$$

The silica products prepared according to Examples 1–2 were tested according to the aforementioned test methods. The properties obtained from these tests are set forth in Table II below. For comparative purposes, the properties of three prior art silicas available from the J. M. Huber Corporation, Edison, N.J. are also set forth in Table II.

TABLE II

|  | Example 1 | Example 2 | Zeodent® 113 | Zeodent® 215 | Zeodent® 115 |
|---|---|---|---|---|---|
| 5% pH | 7.1 | 7.2 | 7.3 | 7.0 | 7.1 |
| % $Na_2SO4$ | 1.61 | 1.92 | 0.35 | 0.55 | 1.14 |
| Oil absorption, ml/100 g | 116 | 103 | 86 | 88 | 93 |
| % Transmittance | 84.8 | 86.4 | 61 | 80.1 | 86.8 |
| Refractive Index | 1.445 | 1.441 | 1.438 | 1.441 | 1.451 |
| Median particle size, $\mu$m | 11.4 | 11.8 | 9.8 | 10.5 | 10.7 |
| Einlehner Abrasion, mg/100,000 revolutions | 2.06 | 3.03 | 5.65 | 6.23 | 4.11 |
| Brightness | 98.6 | 98.5 | 98.6 | 98.5 | 98.4 |
| % Moisture | 9.9 | 8.0 | 7.2 | 9.8 | 8.3 |
| % 325 residue | 1.59 | 0.30 | 0.50 | 0.50 | 0.28 |

As can be seen in Table II, the silicas prepared in Examples 1–2 met all the criteria for producing a transparent toothpaste (viz., each had a low index of refraction and high degree of light transmittance) while also being sufficiently hard or abrasive to produce a toothpaste with acceptable or good cleaning performance. As can also be seen, the three prior art silicas have good optical properties for being incorporated into a transparent toothpaste at some water levels, but have generally inferior oil absorption values, which means that they provide poor viscosity build.

To demonstrate their efficacy in consumer products, the silica abrasives of Examples 1–2 were incorporated as powders into six different toothpaste compositions (numbers 4, 5, 9, 10, 13 and 14), which are set forth in Tables III, IV and V, below. Table III compositions contain 10% water, Table IV compositions contain 12% water and Table V compositions contain 13% water. The performance of these compositions was then compared with the performance of toothpaste compositions containing Zeodent® 113, Zeodent® 215, and Zeodent® 115 prior art silica abrasives from the J. M. Huber Corporation. These toothpaste compositions are set forth in Tables III, IV and V. Toothpaste compositions 1, 6 and 11 contain Zeodent® 113 silica abrasive; toothpaste compositions 2, 7 and 12 contain Zeodent® 215 silica abrasive; and toothpaste compositions 3 and 8 contain Zeodent® 115 silica abrasive.

These toothpaste compositions were prepared as follows. A first mixture was formed by combining the following components: glycerin, sorbitol, polyethylene glycol (CARBOWAX 600, from the Union Carbide Corporation, Danbury, Conn.), carboxymethylcellulose (CMC-7MXF, from the Aqualon division of Hercules Corporation, Wilmington, Del.), and then stirring the first mixture until the components dissolved. A second mixture was formed by combining the following components: deionized water, sodium saccharin, tetrasodium pyrophosphate, sodium fluoride, and then stirring until the components are dissolved. The first and second mixtures were then combined while stirring. Thereafter, color is added to the combined mixture with stirring to form a "premix".

The premix was placed into a Ross mixer (model 130LDM, Charles Ross & Co., Haupeauge, N.Y.), silica thickener and silica abrasive added to the premix, and the premix mixed without vacuum. Then 30 inches of vacuum was drawn and each sample mixed for 15 minutes, and then sodium lauryl sulfate and flavor was added. The resulting mixture was stirred for 5 minutes at a reduced mixing speed.

The fourteen different toothpaste compositions were prepared according to the following formulations set forth in Table III–V, below, wherein the amounts are gram units:

TABLE III

| Ingredients | Composition Number | | | | |
|---|---|---|---|---|---|
| | 1 | 2 | 3 | 4 | 5 |
| Glycerin, 99.5% | 25.000 | 25.000 | 25.000 | 25.000 | 25.000 |
| Sorbitol, 70.0% | 35.107 | 35.107 | 35.107 | 35.107 | 35.107 |
| Deionized Water | 10.000 | 10.000 | 10.000 | 10.000 | 10.000 |
| Carbowax 600 | 3.000 | 3.000 | 3.000 | 3.000 | 3.000 |
| CMC-7MXF | 0.400 | 0.400 | 0.400 | 0.400 | 0.400 |
| Tetrasodium Pyrophosphate | 0.500 | 0.500 | 0.500 | 0.500 | 0.500 |
| Sodium Saccharin | 0.200 | 0.200 | 0.200 | 0.200 | 0.200 |
| Sodium Fluoride | 0.243 | 0.243 | 0.243 | 0.243 | 0.243 |
| Zeodent ® 165 silica thickener | 5.500 | 5.500 | 5.500 | 5.500 | 5.500 |
| Zeodent ® 113 silica abrasive | 18.000 | 0.00 | 0.00 | 0.00 | 0.00 |
| Zeodent ® 215 silica abrasive | 0.00 | 18.000 | 0.00 | 0.00 | 0.00 |
| Zeodent ® 115 silica abrasive | 0.00 | 0.00 | 18.00 | 0.00 | 0.00 |
| Example 1 silica abrasive | 0.00 | 0.00 | 0.00 | 18.000 | 0.00 |
| Example 2 silica abrasive | 0.00 | 0.00 | 0.00 | 0.00 | 18.000 |
| FD&C Blue #1, 1.00% Soln. | 0.200 | 0.200 | 0.200 | 0.200 | 0.200 |
| Sodium Lauryl Sulfate | 1.200 | 1.200 | 1.200 | 1.200 | 1.200 |
| Flavor | 0.650 | 0.650 | 0.650 | 0.650 | 0.650 |

TABLE IV

| Ingredients | Composition Number | | | | |
|---|---|---|---|---|---|
| | 6 | 7 | 8 | 9 | 10 |
| Glycerin, 99.5% | 25.000 | 25.000 | 25.000 | 25.000 | 25.000 |
| Sorbitol, 70.0% | 33.170 | 33.107 | 33.107 | 33.107 | 33.107 |
| Deionized Water | 12.000 | 12.000 | 12.000 | 12.000 | 12.000 |
| Carbowax 600 | 3.000 | 3.000 | 3.000 | 3.000 | 3.000 |
| CMC-7MXF | 0.400 | 0.400 | 0.400 | 0.400 | 0.400 |
| Tetrasodium Pyrophosphate | 0.500 | 0.500 | 0.500 | 0.500 | 0.500 |
| Sodium Saccharin | 0.200 | 0.200 | 0.200 | 0.200 | 0.200 |
| Sodium Fluoride | 0.243 | 0.243 | 0.243 | 0.243 | 0.243 |
| Zeodent ® 165 silica thickener | 5.500 | 5.500 | 5.500 | 5.500 | 5.500 |
| Zeodent ® 113 silica abrasive | 18.000 | 0.00 | 0.00 | 0.00 | 0.00 |
| Zeodent ® 215 silica abrasive | 0.00 | 18.000 | 0.00 | 0.00 | 0.00 |
| Zeodent ® 115 silica abrasive | 0.00 | 0.00 | 18.000 | 0.00 | 0.00 |
| Example 1 silica abrasive | 0.00 | 0.00 | 0.00 | 18.000 | 0.00 |
| Example 2 silica abrasive | 0.00 | 0.00 | 0.00 | 0.00 | 18.000 |
| FD&C Blue #1, 1.00% Soln. | 0.200 | 0.200 | 0.200 | 0.200 | 0.200 |
| Sodium Lauryl Sulfate | 1.200 | 1.200 | 1.200 | 1.200 | 1.200 |
| Flavor | 0.650 | 0.650 | 0.650 | 0.650 | 0.650 |

TABLE V

| Ingredients | Composition Number | | | |
|---|---|---|---|---|
| | 11 | 12 | 13 | 14 |
| Glycerin, 99.5% | 25.000 | 25.000 | 25.000 | 25.000 |
| Sorbitol, 70.0% | 32.107 | 32.107 | 32.107 | 32.107 |
| Deionized Water | 13.000 | 13.000 | 13.000 | 13.000 |
| Carbowax 600 | 3.000 | 3.000 | 3.000 | 3.000 |
| CMC-7MXF | 0.400 | 0.400 | 0.400 | 0.400 |
| Tetrasodium Pyrophosphate | 0.500 | 0.500 | 0.500 | 0.500 |
| Sodium Saccharin | 0.200 | 0.200 | 0.200 | 0.200 |
| Sodium Fluoride | 0.243 | 0.243 | 0.243 | 0.243 |
| Zeodent ® 165 silica thickener | 5.500 | 5.500 | 5.500 | 5.500 |
| Zeodent ® 113 silica abrasive | 18.000 | 0.00 | 0.00 | 0.00 |
| Zeodent ® 215 silica abrasive | 0.00 | 18.000 | 0.00 | 0.00 |
| Example 1 silica abrasive | 0.00 | 0.00 | 18.000 | 0.00 |
| Example 2 silica abrasive | 0.00 | 0.00 | 0.00 | 18.000 |
| FD&C Blue #1, 1.00% Soln. | 0.200 | 0.200 | 0.200 | 0.200 |
| Sodium Lauryl Sulfate | 1.200 | 1.200 | 1.200 | 1.200 |
| Flavor | 0.650 | 0.650 | 0.650 | 0.650 |

After toothpaste compositions 1–14 were prepared as above, properties relating to the gel toothpaste clarity, such as refractive index, clarity and haze were determined as follows.

The toothpaste refractive index was measured by taking a drop of toothpaste and placing on an Abbe 60 Refractometer Model 10450, and the refractive index is directly read.

Clarity is a subjective measurement, wherein a ribbon of toothpaste is squeezed onto a sheet of white paper containing typed text. A score of 10 is given if the text can be read perfectly, a score of 1 when the text cannot be seen and intermediate scores of 2 to 9 for progressively better clarity of the text. A score of 8 or better is deemed a good clear gel toothpaste, indicating the silica abrasive is transparent. Typically, a toothpaste clarity rating of 10 will have a corresponding haze value (described below) of less than 40; clarity rating of 9, a haze value of about 45–55; a clarity rating of 8, a haze value of about 55–65; and a clarity rating of 7, a haze value of about 65–70.

The "haze value" of the clear gel toothpaste is measured by light transmission utilizing a Gardner XL-835 Colorimeter. The instrument is first calibrated according to the manufacturer's directions. Next, two microscope slides, having dimensions of 38×75 mm, and a thickness 0.96 to 1.06 mm, are placed on a flat surface. One slide is covered with a plexiglass spacer, (38×75 mm, 3 mm thickness, with 24×47 mm open area). The gel toothpaste in squeezed into the open area of the plexiglass spacer. The second slide is placed over the toothpaste and pressure applied, by hand, to eliminate excess toothpaste and air. The sample is placed on the transmission light beam of the pre-calibrated meter and the haze value is recorded from three different specimen locations and averaged. Lower haze values described clearer, transparent toothpastes.

A Brookfield viscometer (Model RVT) with a Helipath stand and spindle T-E is used to determine toothpaste viscosity. The viscometer speed is set at 5 rpm. The toothpaste sample container is placed in a 25° C. water bath to equilibrate. The viscosity is read at three levels and averaged. Results are reported in centipoise (cps).

The results of the refractive index, clarity, and haze value measurements are set forth in table VI, below, along with the water concentration in the toothpaste composition, and the silica abrasive refractive index.

TABLE VI

| Comp. No. | Silica abrasive | Silica RI | Premix RI | Wt % $H_2O$ | Viscosity (Cps) | Clarity | Haze |
|---|---|---|---|---|---|---|---|
| 1 | Zeodent ® 113 | 1.438 | 1.446 | 10 | 420,000 | 6 | 73 |
| 2 | Zeodent ® 215 | 1.441 | 1.446 | 10 | 360,000 | 7 | 68.5 |
| 3 | Zeodent ® 115 | 1.451 | 1.446 | 10 | 530,000 | 7 | 68 |
| 4 | Example 1 | 1.445 | 1.446 | 10 | 570,000 | 9 | 45 |
| 5 | Example 2 | 1.441 | 1.446 | 10 | 450,000 | 9 | 53 |
| 6 | Zeodent ® 113 | 1.438 | 1.442 | 12 | 400,000 | 10 | 29 |
| 7 | Zeodent ® 215 | 1.441 | 1.442 | 12 | 370,000 | 10 | 38 |
| 8 | Zeodent ® 115 | 1.451 | 1.442 | 12 | 440,000 | 6 | 70.4 |
| 9 | Example 1 | 1.445 | 1.442 | 12 | 460,000 | 10 | 28.5 |
| 10 | Example 2 | 1.441 | 1.442 | 12 | 480,000 | 10 | 27.2 |
| 11 | Zeodent ® 113 | 1.438 | 1.441 | 13 | 480,000 | 9 | 51 |
| 12 | Zeodent ® 215 | 1.441 | 1.441 | 13 | 380,000 | 10 | 35 |
| 13 | Example 1 | 1.445 | 1.441 | 13 | 500,000 | 10 | 23 |
| 14 | Example 2 | 1.441 | 1.441 | 13 | 490,000 | 10 | 29 |

Toothpaste compositions 1 through 5 contain 10% water, with the toothpaste premix having a refractive index of 1.446. It is seen from the data above in Table VI that the father the silica refractive index is from the toothpaste premix refractive index, the worse are the optical properties (clarity and haze). Control compositions 1–3, containing prior art silica abrasives, have refractive Indices from 0.005 to 0.008 units from the premix refractive index, while the compositions containing the inventive silica abrasives (compositions 4–5) have refractive indices only 0.001–0.004 units from the premix refractive index. Additionally, the inventive silica abrasives provide excellent toothpaste viscosity build. Only the inventive silicas possess both good optical and provide good viscosity build.

Toothpaste compositions 6 through 10 contain 12% water, with the toothpaste having a refractive index of 1.442. It is seen from the data above in Table VI that toothpaste composition 8, containing Zeodent 115 prior art silica abrasive, has a refractive index 9 units from the toothpaste premix refractive index, resulting in poor toothpaste clarity and haze. Compositions 6 and 7 (containing prior art silica abrasives) and compositions 9 and 10 (containing the inventive silica abrasives of Examples 1–2) have good toothpaste optical properties, since the silica abrasives' refractive indices closely match the premix. However, the inventive silica abrasives provide more viscosity build than the prior art silica abrasives. Only the inventive silicas possess both good optical and viscosity build properties.

Toothpaste compositions 11 through 14 contain 13% water, with the toothpaste premix having a refractive index of 1.441. All of these compositions have good toothpaste optical properties, since the silica abrasives' refractive indices closely match the premix. The inventive silica abrasives do provide less haze than the prior art silica abrasives, particularly as compared to composition 11. Additionally, the inventive silica abrasives provide more viscosity build than the prior art silica abrasives. Only the inventive silicas possess both good optical and viscosity build properties.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A transparent dentifrice comprising:
   from about 10 wt % to about 13 wt %, based on the weight of the dentifrice, of water;
   an abrasive, low-structure, precipitated silica having:
      a refractive index of from about 1.439 to 1.450;
      an oil absorption of from about 90 mL/100 g to about 120 ml/100 g;
      a light transmittance of greater than about 60%; and
      a Brass Einlehner abrasion value of less than about 3.03 mg loss/100,000 rev.;
   wherein the dentifrice has:
      a haze value of less than about 50;
      an RDA of about 50 to 200; and
      a refractive index of from about 1.439 to 1.450.

2. The dentifrice according to claim 1, wherein the dentifrice has a viscosity of greater than about 425,000 cps.

3. A dentifrice according to claim 1, wherein the dentifrice has a haze value of less than about 35.

4. A transparent dentifrice comprising:
   a) a premix consisting essentially of a non-silica thickening agent, deionized water, and a humectant selected from the group consisting of glycerin, sorbitol, and polyethylene glycol; wherein the premix has a refractive index of from about 1.439 to 1.450; and
   b) about 0.01 wt % to about 35 wt %, based on the weight of the dentifrice, of an abrasive, low-structure, precipitated silica having:
      a refractive index of from about 1.439 to 1.450;
      an oil absorption of from about 90 ml/100 g to about 120 ml/100 g;
      a light transmittance of greater than about 60%; and a Brass Einlehner abrasion value of less than about 3.03 mg loss/100,000 rev.; and c) about 10 wt % to about 13 wt %, based on the weight of the dentifrice, of water;
wherein the dentifrice has an RDA of greater than about 50, a haze value of less than about 50, and a viscosity of greater than about 425,000 cps.

5. A method of preparing a dentifrice comprising the steps of:
a) preparing a premix, the premix containing no silica and having a refractive index of from about 1.439 to 1.450; and
b) mixing the premix with an abrasive, low-structure, preceipitated silica having:
a refractive index of from about 1.439 to 1.450;
an oil absorption of from about 90 ml/100 g to about 120 ml/100 g;
a light transmittance of greater than about 60%; and
a Brass Einlehner abrasion value of less than about 3.03 mg loss/100,000 rev.;
thereby forming a transparent dentifrice having an RDA of greater than about 50; a haze value of less than about 50; and a refractive index of from about 1.439 to 1.450.

6. The method according to claim 5, wherein the dentifrice has a viscosity of greater than about 425,000 cps.

7. The dentifrice according to claim 4, wherein the dentifrice has a refractive index of less than 1.448.

8. The dentifrice according to claim 4, wherein the dentifrice has a haze value of less than about 35.

9. The dentifrice of claim 1 wherein said abrasive, low-structure precipitated silica exhibits a refractive index of from 1.441 to 1.445.

10. The dentifrice of claim 2 wherein said abrasive, low-structure precipitated silica exhibits a refractive index of from 1.441 to 1.445.

11. The dentifrice of claim 7 wherein said abrasive, low-structure precipitated silica exhibits a refractive index of from 1.441 to 1.445.

12. The method of claim 5 wherein said abrasive, low-structure precipitated silica exhibits a refractive index of from 1.441 to 1.445.

13. The method of claim 6 wherein said abrasive, low-structure precipitated silica exhibits a refractive index of from 1.441 to 1.445.

* * * * *